United States Patent [19]

Jaffe

[11] Patent Number: 5,473,093
[45] Date of Patent: Dec. 5, 1995

[54] PROCESS FOR THE SYNTHESIS OF DIETHYL ETHYLPHOSPHONATE

[75] Inventor: Fred Jaffe, Ossining, N.Y.

[73] Assignee: Akzo Nobel N.V., Arnhem, Netherlands

[21] Appl. No.: 370,940

[22] Filed: Jan. 10, 1995

[51] Int. Cl.$^6$ ............................................. C07F 9/40
[52] U.S. Cl. ............................................. 558/88; 558/214
[58] Field of Search ............................................. 558/88

[56] References Cited

U.S. PATENT DOCUMENTS 4,311,652  1/1982  Abramson et al. ...................... 558/88

FOREIGN PATENT DOCUMENTS 713669  8/1954  United Kingdom.

OTHER PUBLICATIONS

"The Reaction Between Trialkyl Phosphites and Alkyl Halides", by A. H. Ford–Moore, Journal of the Chemical Society, 1947, pp. 1465–1467.
"Esters Containing Phosphorus. Part V. Esters of Substituted Phosphonic and Phosphonous Acids.", by B. C. Saunders et al., Journal of the Chemical Society, 1948, Part I, pp. 699–703.
"Diisopropyl Methylphosphonate", submitted by A. H. Ford–Moore, Organic Syntheses, Collective vol. 4, John Wiley & Sons, Inc., 1963, pp. 325–327.
"A Kinetic Study of Michaelis–Arbuzov Reactions", by G. Aksnes et al., Acta Chemica Scandinavica, 18 (1964), 38–46.
"Carbanions Phosphonates α–Lithiés: Synthése, Basicité Comparée et Stabilité À L'Autocondensation", by M.–P. Teulade et al., Journal of Organometallic Chemistry, 312 (1986) 283–295.

*Primary Examiner*—Johann Richter
*Assistant Examiner*—Michael G. Ambrose
*Attorney, Agent, or Firm*—Richard P. Fennelly; Louis A. Morris

[57] ABSTRACT

Diethyl ethylphosphonate is formed by the catalytic rearrangement of triethyl phosphite in a reaction medium at elevated temperature, preferably using an ethyl iodide as the rearrangement catalyst, employing a heel of diethyl ethylphosphonate in the reaction medium when the reaction is begun with maintaining of the reaction medium at a temperature above the boiling point of the triethyl phosphite (for example, a temperature of from about 175° C. to about 185° C.) and addition of the triethyl phosphite to the reaction medium at a rate slow enough to maintain that temperature.

7 Claims, No Drawings

PROCESS FOR THE SYNTHESIS OF DIETHYL ETHYLPHOSPHONATE

BACKGROUND OF THE INVENTION

It is known, in general, to synthesize diethyl ethylphosphonate by the alkylating agent-catalyzed rearrangement of triethyl phosphite at elevated temperature. See, for example, the following references: Journal of The Chemical Society, p. 1466 (1947) and pp. 702–703 (1948); British Patent No. 713,669; Organic Syntheses, Collective Volume 4, p. 326 (1963); Acta Chemica Scandinavica 18 (1964), p.39; and Journal of Organometallic Chemistry, 312 (1986), p. 293. The alkylating agent may be added directly or generated in situ in the reaction medium. Examples of such alkylating agents known to persons of ordinary skill in the art include the alkyl iodides, the alkyl toluene sulfonates, the alkali metal iodides, or iodine itself.

The known procedures of the foregoing type are mainly small scale laboratory preparations. Large scale (i.e, industrial scale) runs could result in a runaway reaction due to the highly exothermic nature of the Arbuzov reaction. Improved safety and less threat to the environment are the beneficial features of the present invention as compared to known laboratory scale preparations.

DESCRIPTION OF THE INVENTION

In accordance with the present invention, diethyl ethylphosphonate is formed by the catalytic rearrangement of triethyl phosphite in a reaction medium at elevated temperature using or generating an alkylating agent, such as ethyl iodide, as the preferred rearrangement catalyst, employing a heel of diethyl ethylphosphonate in the reaction medium when the reaction is begun with maintaining of the reaction medium at a temperature above the boiling point of the triethyl phosphite (for example, a temperature of from about 175° C. to about 185° C.) with the addition of the triethyl phosphite reagent to the reaction medium at a rate slow enough to maintain that temperature.

The triethyl phosphite reagent that is used should be at a minimum of 98% purity and have a low acid number in order to achieve the desired level of purity in the desired diethyl ethylphosphonate product (about 97%–99%) without the need for extensive purification procedures.

The ethyl iodide catalyst which may be selected for use herein, in connection with a preferred embodiment of the invention, has the advantage of producing high yields of product with low levels of impurities and is recyclable. For example, it can be distilled as a forerun along with some diethyl ethylphosphonate product which can be used as a heel in a later reaction procedure. With use of a small head space, relative to the liquid volume in the reactor, and the use of efficient condensation and trapping of volatile ethyl iodide (boiling point =69° to 73° C.), it is deemed that an attractively high recovery and recycle of ethyl iodide is achievable. The ethyl iodide has the advantage of not generating by-products from the reaction at the approximate levels of catalyst use as do other known catalysts for the reaction, such as methyl iodide, methylene iodide, elemental iodine, ethylene bromide, or ethyl toluene sulfonate. A catalyst level of about 2.2%, by weight of triethyl phosphite, was judged as an especially preferred level for use for rapid reaction and convenient reaction time. Lower levels (e.g., down to about 0.5%), however, can be used although the reaction time will be increased and the acid number of the product may be slightly elevated (e.g., above 1.0 mg KOH/g as compared to 0.4 mg KOH/g for a 2.2% catalyst level). The use of such lower levels of catalyst will, however, have the advantage of lowering the cost of producing the product in view of the relatively high cost of the catalyst. Higher levels of catalyst increase the reaction rate but are not economical due to the comparatively high cost of catalyst.

The amount of diethyl ethylphosphonate which should be charged as a heel is preferably in the neighborhood of 20% to 25% of the amount of triethyl phosphite that is used although higher and lower levels can be used. This heel allows for control of reaction temperature above the boiling point of the triethyl phosphite. Control of the exothermic reaction is achieved by the low level of catalyst used.

The reaction can take place over a period of from about five to ten hours at the above described temperature and catalyst level. A post heating for about two hours at that temperature after addition of the triethyl phosphite will complete the reaction. The rate of rearrangement of the triethyl phosphite to the desired product is deemed to be a function of catalyst concentration and temperature. Control of the triethyl phosphite addition rate to maintain the temperature in the desired range (most preferably at about 180° C.) insures that no appreciable phosphite buildup will occur with a concomitant drop in the reaction temperature (due to the lower 156° C. boiling point of the triethyl phosphite).

Arbuzov rearrangement reactions of the type described herein are exothermic as a high energy tertiary phosphite is converted to a much more stable tetracoordinated pentavalent phosphorus structure. The rate of heat generated during the reaction is controlled by the reaction temperature, the catalyst level used, and the rate of addition of the triethyl phosphite reagent. This automatically avoids a runaway reaction. If the rate of phosphite addition is too fast, the temperature and therefore the reaction rate decreases. Very slow addition rates simply extend the reaction time. For optimum production, the addition rate needs to be kept in balance with the cooling capacity of the reaction vessel so that the cooling capacity is sufficient to remove the heat of condensation of triethyl phosphite in order to condense the triethyl phosphite and prevent loss of the reactant. In the event of loss of cooling water in an open system, the triethyl phosphite will be lost by vaporization while the low catalyst level will not allow an excessive reaction rate that could lead to a runaway reaction.

It is preferred to recover a bottoms out product after stripping of ethyl iodide and a diethyl ethylphosphonate heel from the reaction medium. An oxidative treatment, such as with chlorine, can be employed, if desired, to insure removal of any unreacted triethyl phosphite which remains.

The present invention will be further illustrated by the Examples which follow.

EXAMPLES 1–8

A series of runs was performed in accordance with the present invention for the synthesis of diethyl ethylphosphonate (DEEP). Initially, 30 ml of DEEP was added, as a heel, to a dry, nitrogen-filled, leak-free 250 ml, three-neck round bottom flask equipped with a mechanical stirrer, thermometer, condenser and vacuum take-off head, graduated dropping funnel in a heating mantle. The ethyl iodide (EtI) catalyst was added by means of syringe to the DEEP heel with the amount used in these Examples ranging from 0.75 wt % to 7.5 wt % based on the amount of triethyl phosphite (TEP) to be charged. The TEP (132·gm for a 0.8 mole run) was then placed in the graduated dropping funnel. The temperature of the flask was raised to 180° C. and the TEP addition rate to the flask was adjusted to maintain a reaction temperature of 178° C. to 180° C. Sampling of the reaction mixture was performed when the addition of TEP was completed by cooling the mixture to 25° C. and removing a small sample. Area % data by gas chromatographic analyses, using a TCD detector, was used to monitor the decrease in TEP and the increase in DEEP with time. If TEP was still present, the reaction was continued at 180° C. for one to three hours until no peak for TEP was detected by gas chromatographic analysis. After the reaction was completed, the reaction mixture was cooled and a small portion was analyzed.

To recover the EtI catalyst and simulate isolation of a heel for a following batch reaction, the reaction mixture was stripped at 150° C./180 mm Hg until about 15% of the sample, including all of the EtI, was carried out. The volatiles and the remaining bottoms out product were then analyzed.

The Table which follows shows the results that were obtained:

0.34 area % DEP, and 0.54 area % TEPO.

In particular, this invention is not limited to the choice of a particular catalyst. The safety features apply to any satisfactory catalyst for the rearrangement. Catalytic additives that generate ethyl iodide or other ethylating reagents are intended to be included. The self limiting reaction rate resulting from the appropriate choice of reaction temperature and catalyst level (to provide an acceptable reaction rate) is the main safety feature.

The foregoing Examples should not be construed in a limiting sense since they are intended to merely illustrate certain embodiments of the invention. The scope of protection sough is set forth in the claims which follow.

I claim:

1. In a process for forming diethyl ethylphosphonate by the alkylating agent-catalyzed rearrangement of triethyl phosphite at elevated temperature, wherein the improvements comprise:

having a heel of diethyl ethylphosphonate in the reaction medium when the reaction is begun;

| | ACA 5813 | | | | | | | |
|---|---|---|---|---|---|---|---|---|
| | EtI | TEP | TEP Addn | Total Rxn | GC Wt % | | | |
| Example No. | (Wt %) | (Moles) | Time (hrs) | Time (hrs) | DEEP | DEP | TEPO | Acid No. |
| 1 | 2.3 | 0.8 | 2.0 | 4.25 | 97.8 | 1.5 | 0.7 | — |
| 2 | 2.3 | 0.8 | 1.75 | 3.75 | 98.2 | 0.9 | 0.9 | 2.1 |
| 3 | 2.2 | 0.8 | 3.25 | 5.25 | 98.5$^A$ | 0.6$^A$ | 0.9$^A$ | 2.4 |
| 4* | 2.2 | 8.0 | 3.0 | 5.0 | 98.1 | 1.0 | 0.9 | 0.6 |
| 5 | 1.2 | 0.8 | 4.75 | 7.0 | 97.8 | 0.6 | 1.6 | 3.9 |
| 6$^C$ | 0.73 | 0.8 | 5.25 | 10.5$^C$ | 97.4$^{A,B}$ | 0.7$^{A,B}$ | 2.0$^{A,B}$ | — |
| 7 | 0.75 | 0.8 | 5.25 | 9.0 | 96.5 | 0.9 | 2.6 | 0.9 |
| 8 | 3.75 | 0.8 | 2.5 | 5.5 | 99.0$^B$ | ND$^B$ | 0.0$^B$ | — |

*In Example 4, the stripped bottoms out product contained 98.2% DEEP, 0.7% DEP, and 1.1% TEPO (triethyl phosphate), while the chlorine treated product contained 98.98% DEEP, had no detectible DEP, and contained 1.1% TEPO. The distilled DEEP from Example 4 contained 98.6% DEEP, 0.7% DEP, and 0.7% TEPO (gc area % data obtained with a thermal conductivity detector).
$^A$ = Data is for the unstripped reaction product.
$^B$ = GC Area % data was obtained using a thermal conductivity detector.
$^C$ = This reaction was completed after eight hours total reaction time and showed no change in area % composition over the next two hours.

EXAMPLE 9

This Example illustrates preparation of a DEEP heel for use in the type of process shown in Examples 1–8.

One gram of EtI was added to 30 gm of TEP at room temperature, and the temperature was increased to 150° C. over twenty-five minutes. A sample of product was removed for analysis. It contained 92.7 area % TEP, 6.4 area % DEEP, 0.47 area % DEP, and 0.42 area % TEPO. Then, an additional 0.5 gm of EtI was added by syringe at 150° C., and heating at 150° C. was continued for an additional forty minutes. Another analyzed sample, at this point in the reaction, showed that the TEP content had decreased to 32.4 area %, that the DEEP content increased to 66.8 area % and the DEP and TEPO contents were 0.40 and 0.37 area %, respectively. Additional EtI (1.6 gm) was added and the heating at 150° C. was continued for an additional hour. The sample taken at that point contained 98.4 area % DEEP, 0.75 area % TEP, 0.32 area % DEP, and 0.50 area % TEPO. After an additional hour of heating at 150° C. another sample showed no detectible TEP and contained 99.1 area % DEEP, maintaining the reaction medium at a temperature above the boiling point of the triethyl phosphite; and adding the triethyl phosphite to the reaction medium at a rate slow enough to maintain that temperature.

2. A process as claimed in claim 1 wherein the temperature is maintained at from about 175° C. to about 185° C.

3. A process as claimed in claim 1 wherein ethyl iodide is present, as catalyst, at from about 0.5 wt % to about 10 wt % of the triethyl phosphite.

4. A process as claimed in claim 1 wherein the temperature is maintained at from about 175° C. to about 185° C. and ethyl iodide is present, as catalyst, at from about 1 to about 5 wt % of the triethyl phosphite.

5. A process as claimed in claim 1 wherein the amount of diethyl ethylphosphonate present as a heel in the reaction medium ranges from about 20% to about 25%, by weight of triethyl phosphite.

6. A process as claimed in claim 2 wherein the amount of diethyl ethylphosphonate present as a heel in the reaction medium ranges from about 20% to about 25%, by weight of triethyl phosphite and the temperature is maintained at from about 175° C. to about 185° C.

7. A process as claimed in claim 1 wherein the amount of diethyl ethylphosphonate present as a heel in the reaction medium ranges from about 20% to about 25%, by weight of triethyl phosphite, the temperature is maintained at from about 175° C. to about 185° C., and ethyl iodide is present, as catalyst, at from about 2% to about 2.5 wt % of the triethyl phosphite.

* * * * *